(12) United States Patent
Holmqvist (10) Patent No.: US 9,345,844 B2
(45) Date of Patent: May 24, 2016

(54) MEDICAMENT DELIVERY DEVICE (75) Inventor: Anders Holmqvist, Värmdö (SE)

(73) Assignee: SHL Group AB, Nacka Strand (SE)

( * ) Notice: Subject to any disclaimer, the term of this patent is extended or adjusted under 35 U.S.C. 154(b) by 359 days.

(21) Appl. No.: 13/885,901

(22) PCT Filed: Nov. 18, 2011

(86) PCT No.: PCT/SE2011/051392
§ 371 (c)(1),
(2), (4) Date: May 16, 2013

(87) PCT Pub. No.: WO2012/067584
PCT Pub. Date: May 24, 2012

(65) Prior Publication Data
US 2013/0237926 A1    Sep. 12, 2013

Related U.S. Application Data

(60) Provisional application No. 61/415,082, filed on Nov. 18, 2010.

(30) Foreign Application Priority Data

Nov. 18, 2010 (SE) ........................ 1051213

(51) Int. Cl.
*A61M 5/315* (2006.01)
*A61M 5/32* (2006.01)
(Continued)

(52) U.S. Cl.
CPC ............... *A61M 5/3293* (2013.01); *A61M 5/19* (2013.01); *A61M 5/2448* (2013.01); *A61M 5/284* (2013.01); *A61M 5/31596* (2013.01); *A61M 5/326* (2013.01); *A61M 5/3243* (2013.01)

(58) Field of Classification Search
CPC ............ A61M 5/3243; A61M 5/3293; A61M 5/19–5/20; A61M 2005/2013; A61M 2005/208; A61M 5/2066
See application file for complete search history.

(56) References Cited

U.S. PATENT DOCUMENTS 8,276,583 B2    10/2012    Farieta et al.
2009/0270804 A1*   10/2009    Mesa et al. .................... 604/111
(Continued)

FOREIGN PATENT DOCUMENTS

GB          2437924 A        11/2007
WO       03/077968 A2        9/2003
(Continued)

OTHER PUBLICATIONS

Sweden Patent Office, Written Opinion in PCT/SE2011/051392, Feb. 21, 2012.
(Continued)

*Primary Examiner* — Nathan R Price
*Assistant Examiner* — Melissa A Snyder
(74) *Attorney, Agent, or Firm* — Piedmont Intellectual Property (57) ABSTRACT

Medicament delivery device comprising a housing (10) and container holder (12) accommodating a multi-chamber medicament container wherein said housing and said medicament container holder are interactively connected to and movable relative each other; a mixing guard mechanism interactively connected to the body for driving the medicament container holder within the housing achieving a reconstitution, wherein the mixing guard mechanism comprises a guard member (34), a force member (52), a guard member locking means (24, 42) whereby, when the reconstitution is achieved, the medicament container holder and the guard member are movable in relation to said housing from a pre-mix position to a mixed position wherein said medicament container holder has been displaced distally in relation to said housing, at which mixed position said guard member locking means is activated, whereby said guard member is forced in the proximal direction by said force member for covering the delivery member (22).

11 Claims, 7 Drawing Sheets

(51) Int. Cl.
 *A61M 5/19* (2006.01)
 *A61M 5/24* (2006.01)
 *A61M 5/28* (2006.01)

(56) References Cited

U.S. PATENT DOCUMENTS

2010/0094214 A1 4/2010 Abry et al.
2011/0224622 A1 9/2011 Karlsson
2011/0251553 A1 10/2011 Ratjen et al.
2012/0029443 A1 2/2012 Holmqvist

FOREIGN PATENT DOCUMENTS

| WO | 2010/081489 A1 | 7/2010 |
| WO | 2010/139675 A1 | 12/2010 |
| WO | 2011/101349 A1 | 8/2011 |
| WO | 2011/101351 A1 | 8/2011 |
| WO | 2012/067582 A1 | 5/2012 |
| WO | 2012/067583 A1 | 5/2012 |

OTHER PUBLICATIONS

Sweden Patent Office, Int'l Search Report in PCT/SE2011/051392, Feb. 21, 2012.

\* cited by examiner

MEDICAMENT DELIVERY DEVICE

TECHNICAL FIELD

The present invention relates to a medicament delivery device and in particular a medicament delivery device utilizing multi-chamber medicament containers that require mixing before drug delivery to a patient.

BACKGROUND OF THE INVENTION

It is becoming more and more common to use multi-chamber medicament containers in medicament delivery devices such as injectors. The reason for this is that the medicament can be stored for much longer time periods without being degraded in comparison with medicament dissolved in some liquid.

Thus the medicament and the liquid are kept in different compartments in the medicament container and are mixed just before use by moving a dividing wall or stopper such that the compartments can communicate with each other.

However, the multi-chamber medicament containers entail more handling steps before a dose of medicament can be injected in that the plunger rod of the injector has to move the stopper or stoppers of the medicament container in order to initiate the mixing.

Another feature of many medicament delivery devices and in particular injectors, is the attachment of a medicament delivery member, in particular an injection needle to a medicament container and then how to avoid unintentional needle sticks. Document WO2010/000559 discloses a medicament delivery device utilizing a multi-chamber medicament container where the mixing is obtained by rotating a medicament container holder, positioned in the proximal housing part, into a distal housing part whereby the stopper of the medicament container is moved against a plunger rod.

In the initial position the proximal end of the medicament container is protruding beyond the proximal housing part, where the latter also acts as a needle shield, such that a medicament delivery device can be attached to the medicament container holder. When the mixing has been performed, the medicament delivery member is drawn into the proximal housing/needle shield. The needle shield is now used for actuating the device in that when a penetration is performed, the needle shield is pushed in the distal direction, whereby it triggers an auto-injection sequence. Thus the needle shield assembly extends almost to the distal end of the device in order to be able to actuate the injection.

However, for some devices it is neither necessary nor desirable to have so many components and functions since they tend to make the devices more complex and more expensive. There is thus room for development of medicament delivery devices.

BRIEF DESCRIPTION OF THE INVENTION

The aim of the present invention is to provide a medicament delivery device that can handle multi-chamber medicament containers in a simple and intuitive but yet safe way.

According to a main aspect of the invention it is characterised by a medicament delivery device according to the features of the independent patent claim. Preferable embodiments of the invention form the subject of the dependent patent claims.

According to a main aspect of the invention it is characterized by a medicament delivery device comprising a body which comprises a housing and a medicament container holder accommodating a multi-chamber medicament container wherein said housing and said medicament container holder are interactively connected to and movable relative each other, the medicament container holder comprising an attachment means for attaching a delivery member; a mixing guard mechanism interactively connected to the body for driving the medicament container holder within the housing achieving a reconstitution; wherein the mixing guard mechanism comprises a guard member operably connected to the medicament container holder; a force member arranged to act on said guard member; a guard member locking means arranged between said guard member and said medicament container holder such that the guard member is locked to the medicament container holder against the force of the force member, whereby, when the reconstitution is achieved, the medicament container holder and the guard member are capable of being moved in relation to said housing from a pre-mix position in which said attachment means protrudes through a proximal end of said guard member for allowing the attachment of a delivery member to a mixed position wherein said medicament container holder has been displaced distally in relation to said housing, at which mixed position said guard member locking means is activated, whereby said guard member is forced in the proximal direction by said force member for covering the delivery member.

According to another aspect of the invention said guard member locking means comprises first engagement members operatively acting on second engagement members arranged to said medicament container holder, which first and second engagement members are activated and released by a proximal area of said housing.

According to a further aspect of the invention said first engagement members comprise resiliently movable hooking arms, wherein said second engagement member comprises a ledge and wherein a proximal end surface of said housing is arranged to move said hooking arms out of engagement with said ledge when moved in contact with said hooking arms.

According to yet another aspect of the invention said mixing guard mechanism comprises first connection means, interactively connecting said housing and said medicament container holder for allowing the medicament container holder to be displaced within the housing.

According to yet a further aspect of the invention said first connection means comprises cooperating threads on said housing and said medicament container.

According to another aspect of the invention it further comprises a second guard member locking means interactively connected to both the medicament container holder and the guard member and arranged to be positioned in a first unlocked state in which the guard member is allowed to be distally displaced compressing said force member such that a proximal part of the delivery member protrudes through the proximal end of the guard member and positioned in a second locked state in which the guard member is locked after the guard member is proximally displaced by said force member and is covering the delivery member.

According to yet another aspect of the invention said second guard member locking means comprises arms with hooks arranged to said medicament container holder and at least one rib having a distally directed end surface arranged to said guard member such that when said guard member is moved proximally, said at least one hook passes an end surface of said at least one rib, thereby preventing subsequent distal displacement of said guard member.

According to a further aspect of the invention it comprises drive means arranged within said housing and adapted to drive a stopper positioned within said multi-chamber container.

According to yet a further aspect of the invention said drive means comprises a plunger rod and a force member operatively acting on said plunger rod for urging it in the proximal direction.

According to another aspect of the invention it further comprises a holding means for holding said drive means in a pre-tensioned state.

According to yet another aspect of the invention it further comprises activation means capable of acting on said holding means for releasing the drive means from the pre-tensioned state.

According to a further aspect of the invention the device is an injection device.

There are a number of advantages with the present invention. The use of locking function between the guard member and the medicament container holder enables a full view of the medicament delivery member during the whole mixing sequence, whereby the user can positively verify that mixing and accompanying priming is performed. It is also possible to attach a medicament delivery member at any moment during the mixing sequence.

Further, the mixing guard mechanism enables a pushing of the tubular guard member in the distal direction when the device is pressed against a dose delivery site. This movement of the tubular guard member causes components of the mixing guard mechanism to be moved and thus prepared for a locking of the tubular guard member when the device is removed from the dose delivery site after completed dose delivery, whereupon the tubular guard member is pushed in the proximal direction by the spring force, thereby surrounding the medicament delivery member in a locked state, whereby the medicament delivery member cannot be tampered with.

These and other aspects of and advantages with the present invention will become apparent from the following detailed description of the invention and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

In the present application, when the term "distal part/end" is used, this refers to the part/end of the delivery device, or the parts/ends of the members thereof, which is/are located the furthest away from the medicament delivery site. Correspondingly, when the term "proximal part/end" is used, this refers to the part/end of the delivery device, or the parts/ends of the members thereof, which, is/are located closest to the medicament delivery site.

FIGS. 1-7 show an embodiment of the present invention. The device shown comprises a housing having a distal housing part 10 and a proximal housing part 12. The two housing parts are connected to each other via threads where the distal housing part 10 is arranged with threads 14 on its inner surface, FIG. 2, while the proximal housing part 12 is provided with corresponding threads 16 on its outer surface, forming first connection means. The proximal housing part 12 further has an inner compartment 18 designed to accommodate a multi-chamber medicament container 13 as described above, whereby the proximal housing part 12 hereafter will be named medicament container holder 12. This is further arranged with a proximal neck portion 20 arranged with attachment means for attaching a medicament delivery member 22 such as an injection needle as shown. It is however to be understood that other types of delivery members may be employed, such as mouth or nose pieces, nozzles, nebulizers and the like.

Figure 2:
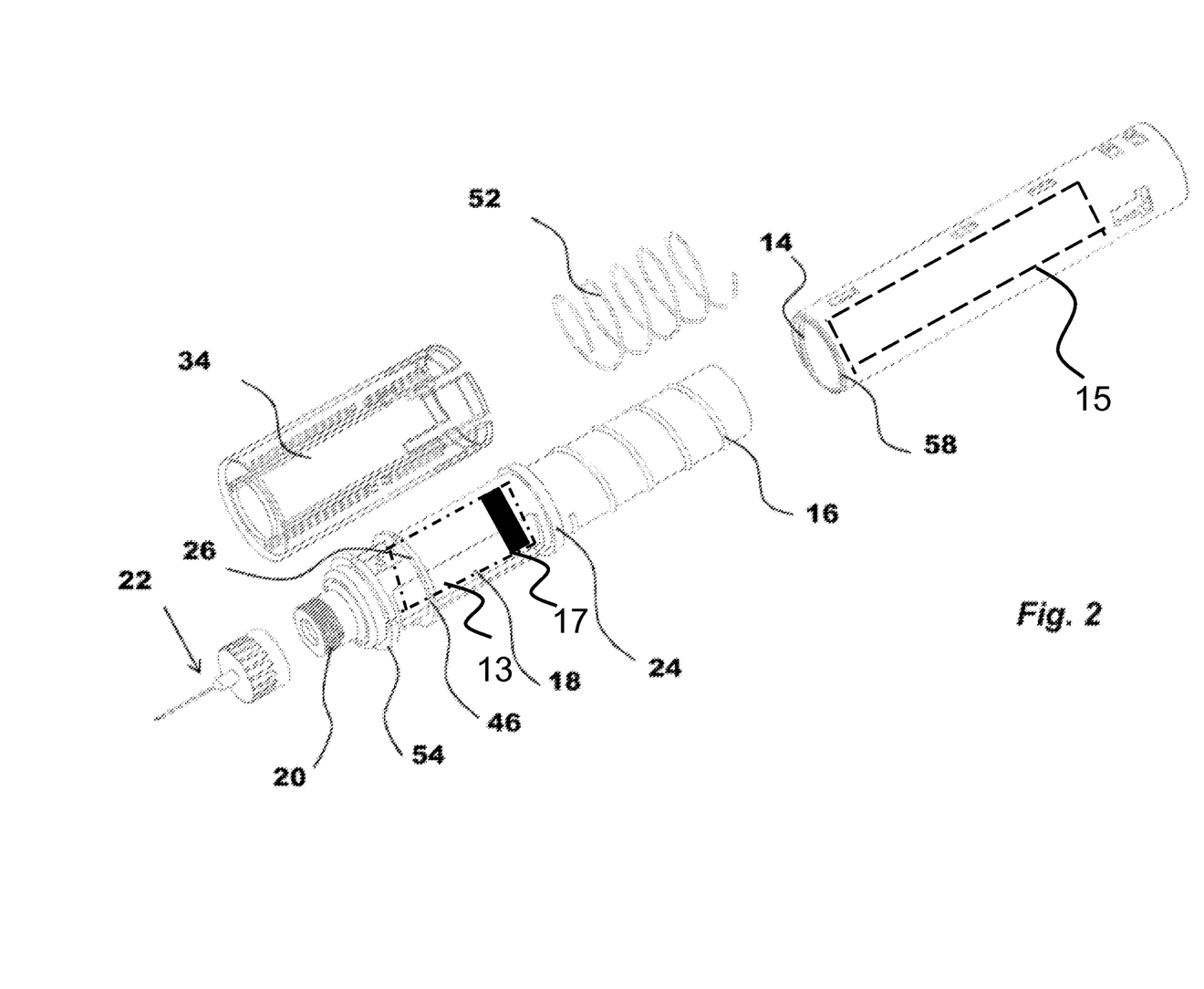
FIG. 2 is an exploded view of the device of FIG. 1.

Further the medicament container holder 12 is arranged with a first and a second circumferential ledge 24, 26, where the first ledge 24 is positioned more distally than the second ledge 26. The proximal end of the proximal housing part 12 is further arranged with at least one distally directed arm 28, FIG. 3, which arm 28 is arranged flexible in a direction transversal to the longitudinal direction of the device. The distal end of the arm 28 is arranged with a ledge or hook 30. Further, adjacent the arm 28 is a guide member 32 pivotally attached to the medicament container holder 12.

Figure 3:
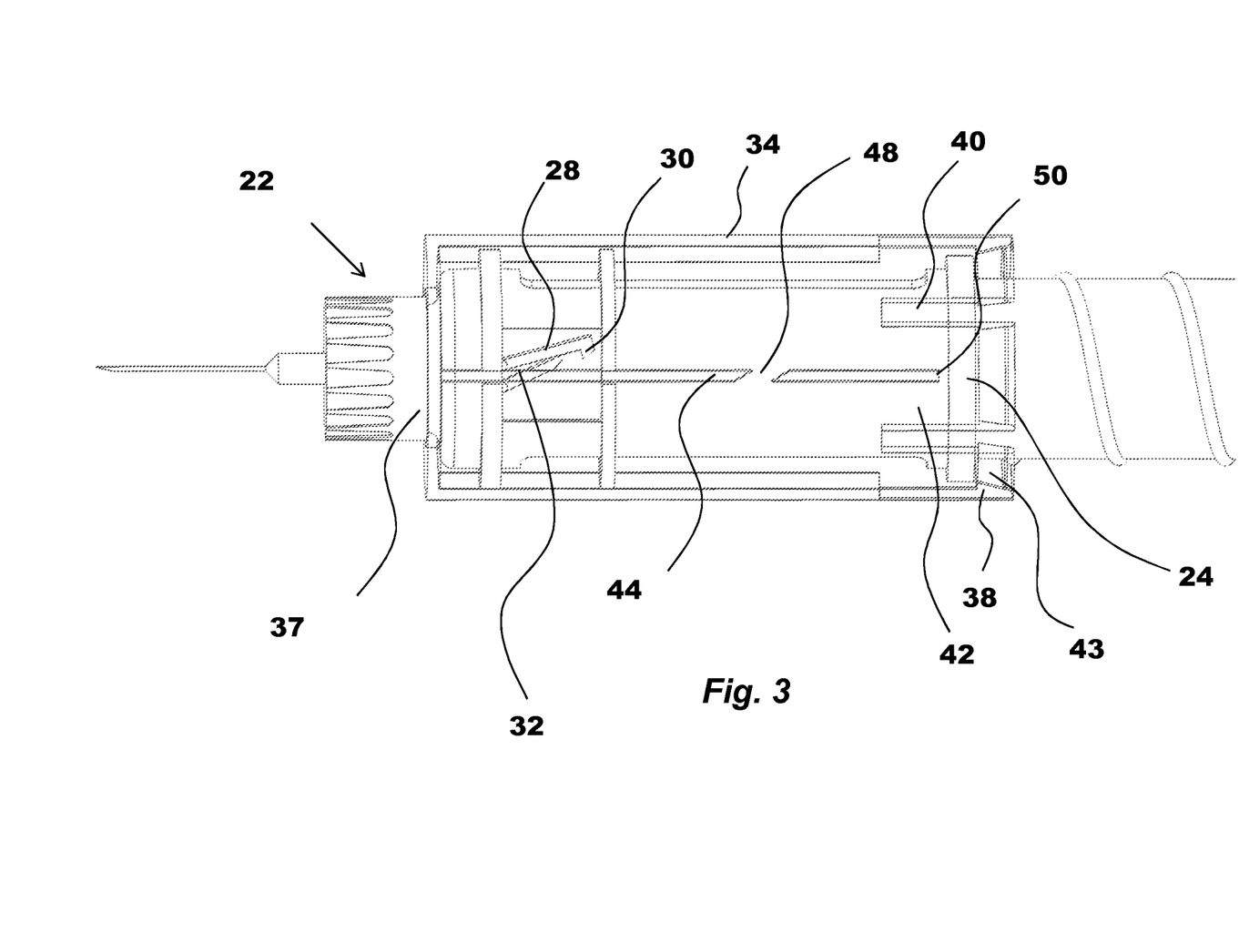
FIG. 3 is a detailed view of the device of FIG. 1 showing a guard member in an initial position.
Figure 4:
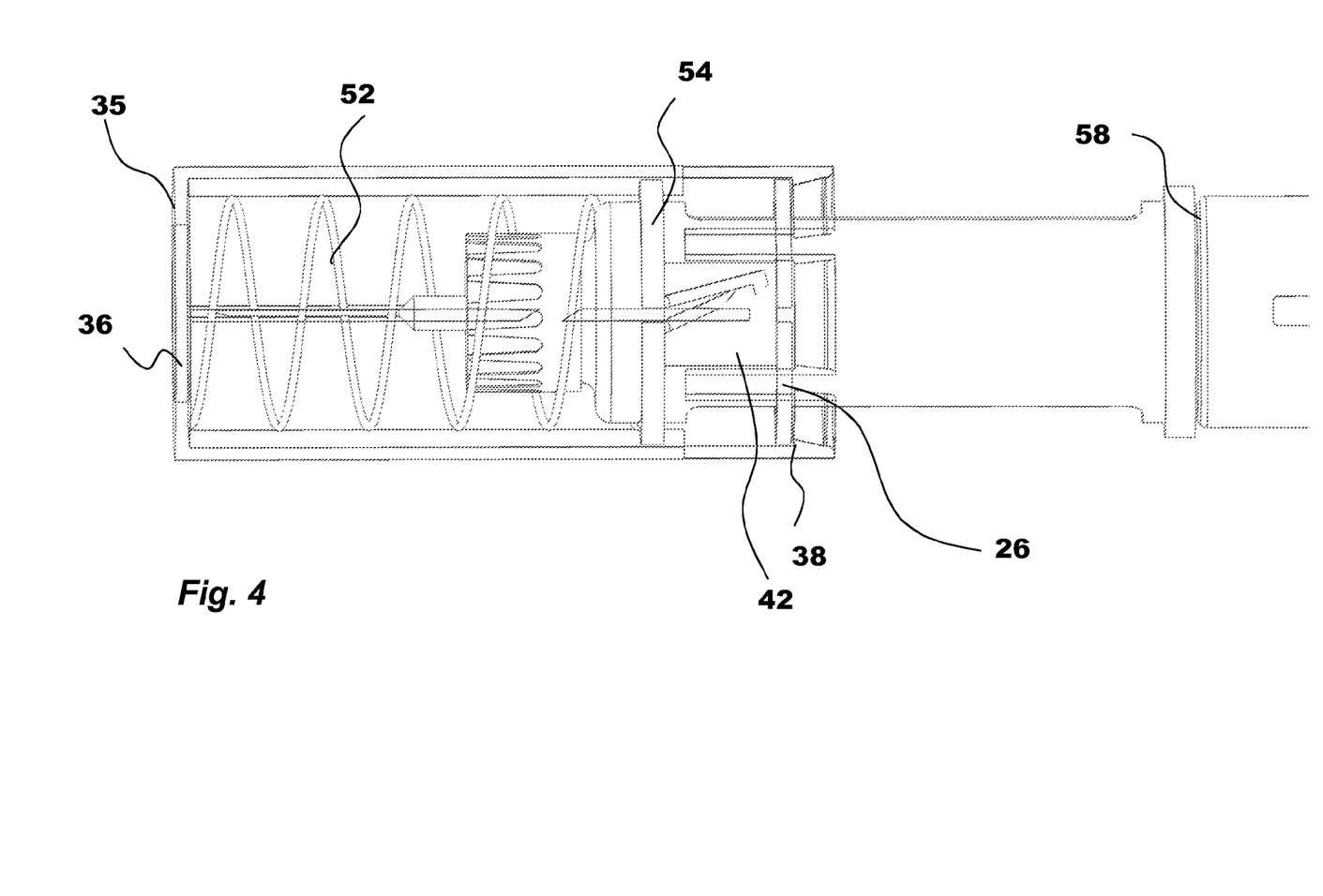
FIG. 4 is a detailed view of the device of FIG. 1 showing the guard member in an extended proximal position.

A medicament delivery guard member 34 is further arranged to the proximal housing part, slidable in relation to the medicament container holder 12. The guard member 34 is designed generally tubular and is provided with a proximal end wall 35, FIG. 4, which end wall 35 is provided with an opening 36 at its proximal end, where the diameter of the opening 36 is somewhat larger than the diameter of an attachment member 37 of the medicament delivery member 22. The circumferential end surface of the distal end of the guard member 34 is arranged with an inwardly directed circumferential ledge 38, FIG. 3. Further the distal end area of the guard member 34 is provided with a number of slits 40, whereby a number of arms 42 are created. Further the ledge 38 is provided with surfaces 43 facing the medicament container holder 12, which surfaces 43 are inclined somewhat in relation to the longitudinal direction of the device. On the inner surface of the guard member, at least one guide rib 44, FIG. 3, is attached, extending in the longitudinal direction of the guard. The guide rib 44 runs in a slit 46, FIG. 2, in the proximal circumferential ledge 26. The guide rib 44 is further arranged with a cut-out 48 at a certain distance from its distal end surface 50, where the surfaces of the cut-out 48 have inclinations in relation to the longitudinal direction of the device. A force member, in the embodiment shown as a spring 52, FIG. 4, is arranged between a circumferential ledge 54 at the proximal end of the medicament container holder 12 and the proximal end wall 35 of the medicament delivery guard member.

Figure 1:
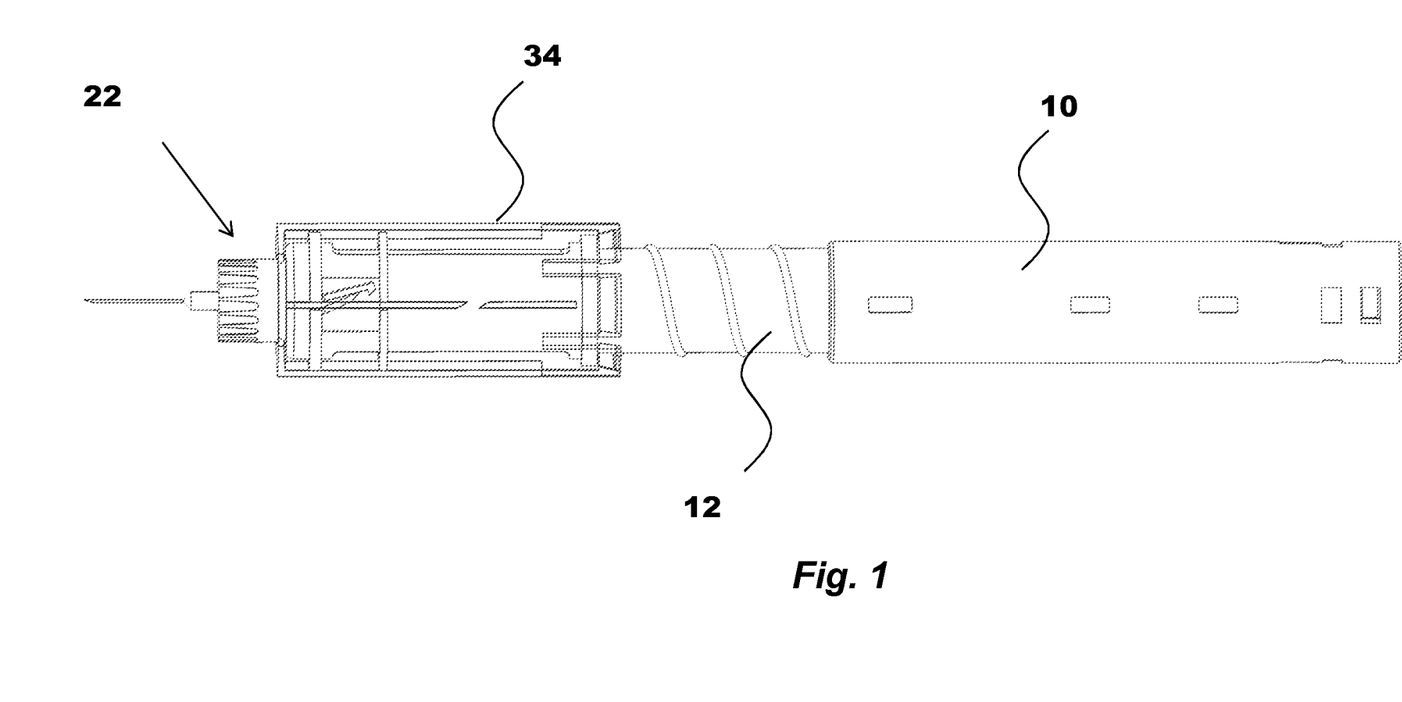
FIG. 1 is a side view of an embodiment of the present invention in an initial position.

The device is intended to function as follows. When the medicament delivery device is delivered to a user, the guard member is in a retracted position as shown in FIG. 1, whereby the neck portion 20 of the medicament container holder 12 protrudes through the proximal opening 36 of the guard member 34. The guard member 34 is held in this retracted position by the ledges 38 of the arms 42 being in contact with a distally directed side surface of the circumferential ledge 24 of the proximal housing part 12. Firstly the user attaches a medicament delivery member 22 on the neck portion 20 of the medicament container holder 12, which is facilitated because the guard member 34 is retracted, thereby exposing the neck portion 20. The guide member 32 is arranged and designed such that it is pressing on the arm 28, whereby they both have an inclined direction in relation to the longitudinal direction of the device, as seen in FIG. 3.

The user is then to perform a mixing or reconstitution of the medicament prior to medicament delivery. He/she then turns the housing parts 10, 12 in relation to each other and the threaded connection 14, 16 between the two parts causes the medicament container holder 12 to be moved into the distal housing part 10. A plunger rod 15 arranged inside the distal housing part 10 then acts on a distal stopper 17 in the medicament container 13, whereby the latter is moved and a mixing of the medicament is performed in a manner known per se. At the end of the mixing movement between the two housing parts, a proximally directed end surface 58, FIGS. 2 and 4, of the distal housing part 10 is moved in contact with the distally directed arms 42 of the guard member 34 whereby the ledges of the arms 42 are pushed radially outwards due to the inclined surfaces 43 that the end surface 58 of the distal housing part acts on.

The radial movement of the arms 42 causes them to move out of contact with the distal ledge 24, whereby the guard member 34 is free to move in the proximal direction due to the force of the spring 52. The medicament delivery member is now covered by the guard member. The movement of the guard member 34 is stopped when the ledges 38 of the arms 42 come in contact with the second circumferential ledge 26 of the medicament container holder 12, FIG. 4.

The next step is then to perform a dose delivery. The user now presses the proximal end of the device with the guard member 34, against the medicament delivery site. The guard member 34 is thereby pushed in the distal direction against the force of the spring 52 whereby the medicament delivery member 22 is exposed through the opening 36 of the guard member 34, FIG. 5. The movement of the guard member 34 causes the guide member 32 to be moved along the rib 44 until it is in position in the cut-out 48, whereby the proximal end surface of the guide member 32 comes in contact with the distally directed surface of the cut-out 48, whereby the guide member is guided to the other side of the rib 44. This in turn causes the arm to flex into a direction generally parallel with the longitudinal direction of the device.

Figure 5:
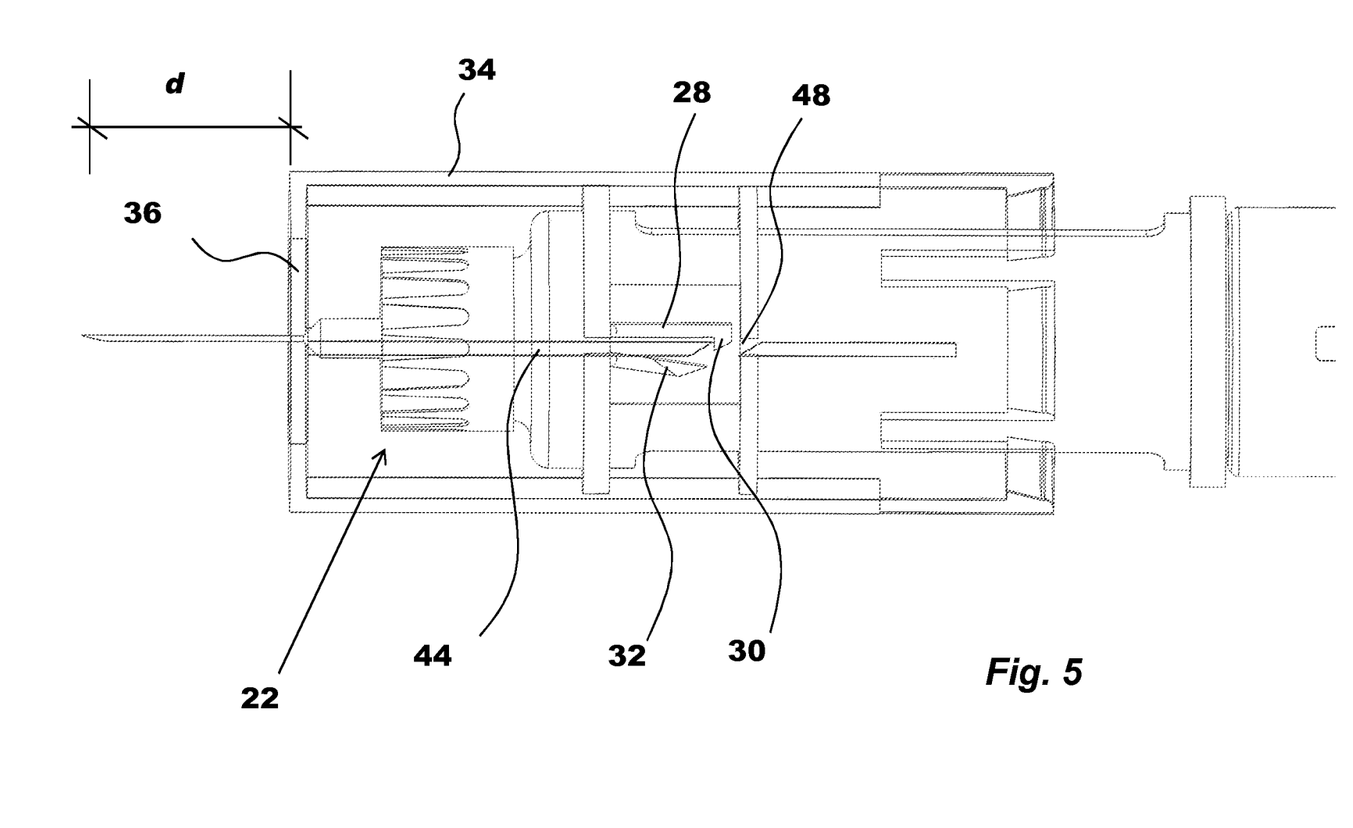
FIG. 5 is a detailed view of the device of FIG. 1 showing the guard member in a retracted position during medicament delivery.
Figure 6:
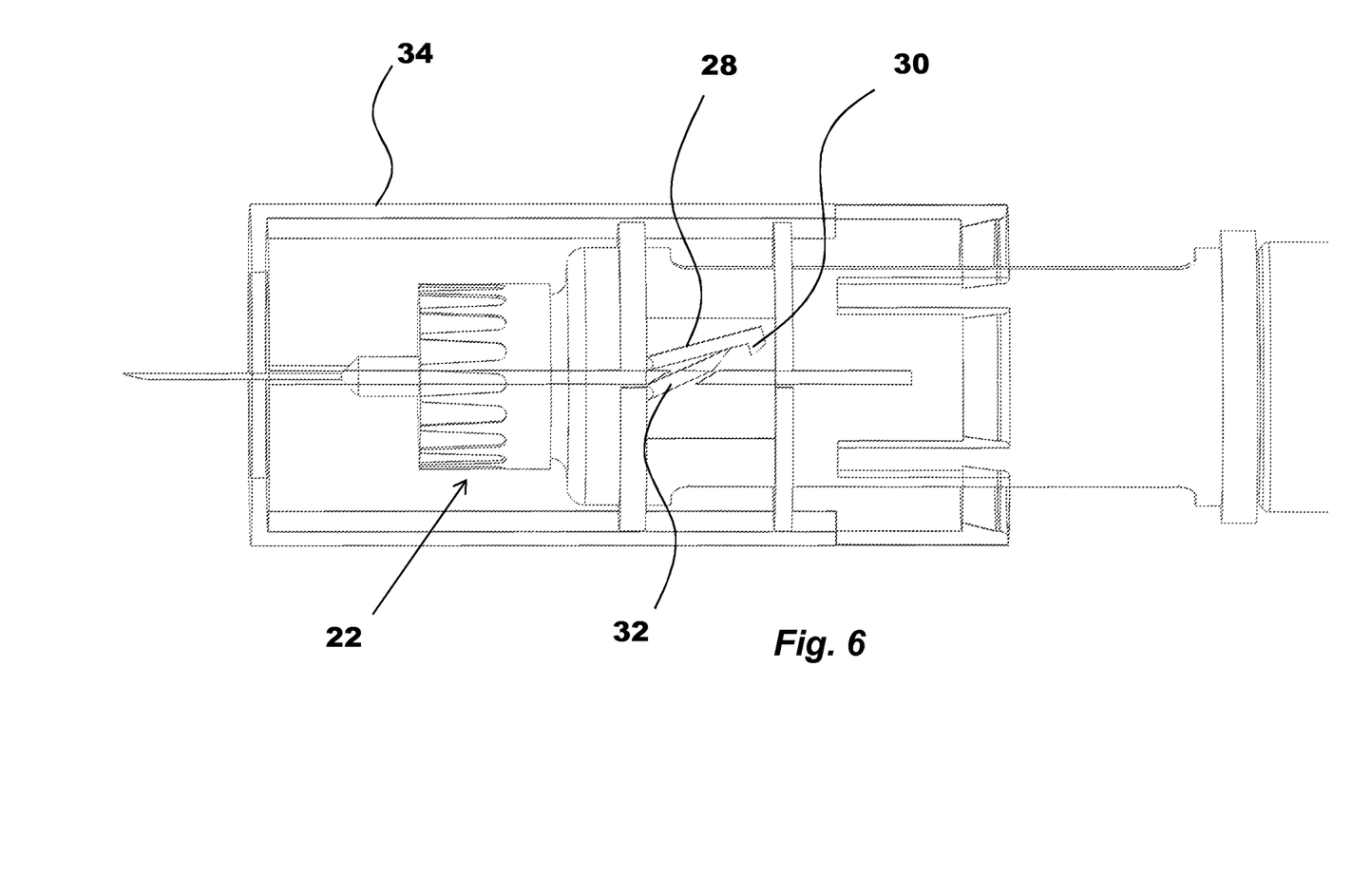
FIG. 6 is a detailed view of the device of FIG. 1 showing the guard member in an intermediate position after medicament delivery.
Figure 7:
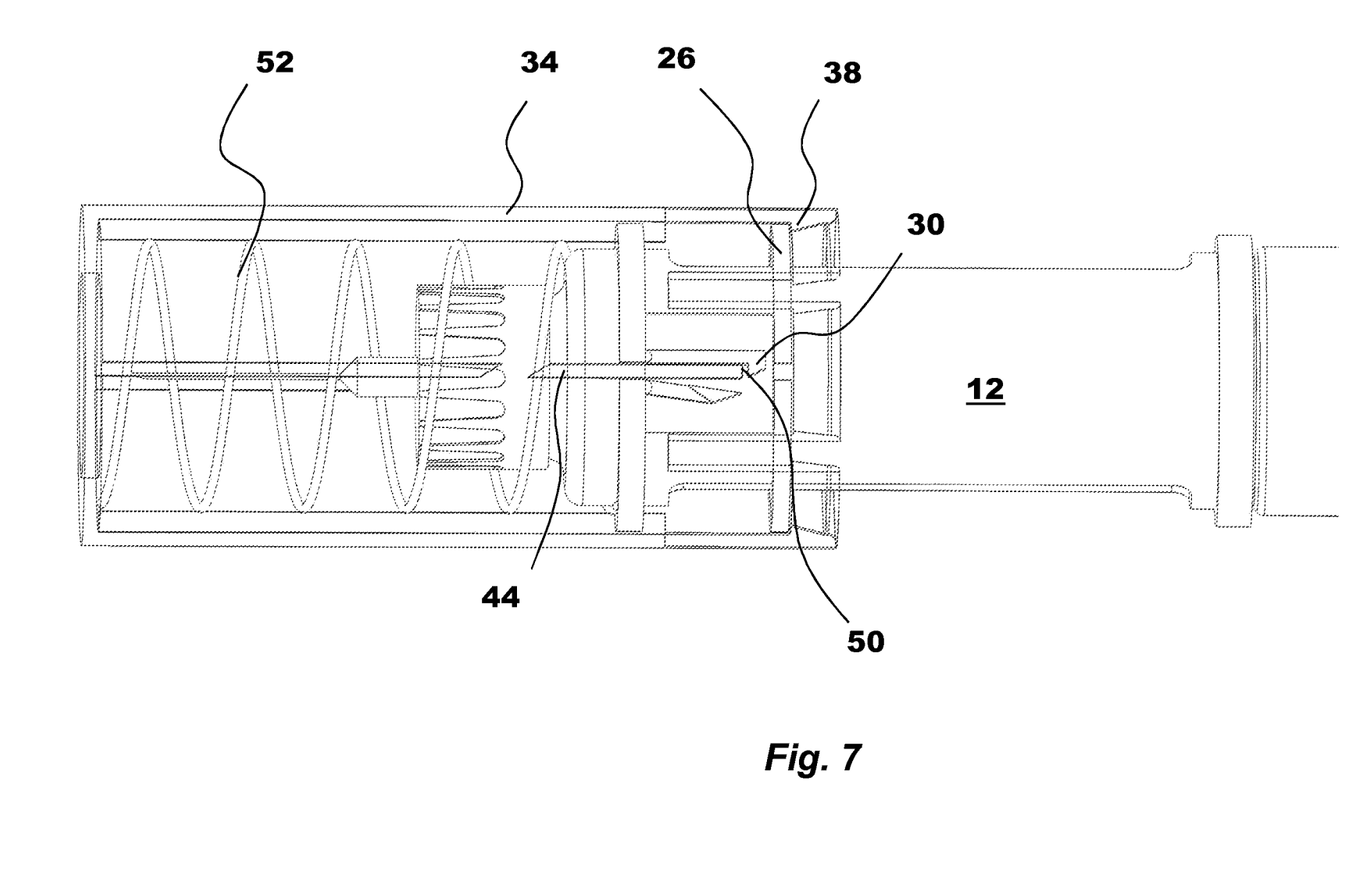
FIG. 7 is a detailed view of the device of FIG. 1 showing the guard member in an extended and locked position.

During the movement of the guard member 34 in the distal direction, the arm 28 and its hook 30 are moved along the rib 44 until the hook 30 is positioned in the cut-out 48, whereby the hook 30 grips the distally directed surface of the cut-out. This stops the guard member 34 from moving further in the distal direction, whereby this stop constitutes the maximum penetration depth d of the device when the medicament delivery member is an injection needle, as shown in FIG. 5.

In this position the medicament delivery is activated by pushing the plunger rod in the proximal direction in order to expel a dose of medicament from the medicament container through the medicament delivery member. The activation could be purely manual, i.e. operated by the user, or automatic, wherein a spring or the like drive member exerts a force on the plunger rod in the proximal direction.

When the dose delivery step has been performed, the device is removed from the medicament delivery site. This causes the guard member 34 to be moved in the proximal direction again due to the force of the spring 52. The arm 28 and its hook 30 now again slide along the rib 44 until the ledges 38 of the guard member 34 are moved in contact with the proximal circumferential ledge 26, whereby the movement is stopped. In this position the hook 30 of the arm 28 has passed the distally directed end surface 50 of the rib, thereby locking the guard member 34 from being pushed in the distal direction, FIG. 7. The medicament delivery member 22 is now safely covered within the guard member 34, thereby preventing accidental needle sticks when the medicament delivery member 22 is an injection needle. The device may now be discarded.

It is to be understood that the embodiment described above and shown in the drawings is to be regarded only as a non-limiting example of the invention and that it may be modified in many ways within the scope of the patent claims.

The invention claimed is:

1. A medicament delivery device, comprising:
a body, comprising a housing and a medicament container holder configured to accommodate a multi-chamber medicament container, wherein the housing and medicament container holder are interactively connected to and movable relative each other, and the medicament container holder comprises an attachment device configured for attaching a delivery member;
a mixing guard mechanism interactively connected to the body for driving the medicament container holder within the housing, thereby achieving a reconstitution;
wherein the mixing guard mechanism comprises:
a guard member operably connected to the medicament container holder;
a force member configured to act on the guard member;
a guard member locking device configured between the guard member and the medicament container holder, wherein the guard member locking device comprises first engagement members operatively acting on second engagement members arranged to the medicament container holder such that the guard member is locked to the medicament container holder against a force of the force member, whereby when the reconstitution is achieved, the medicament container holder and guard member are movable in relation to the housing from a pre-mix position, in which the attachment device protrudes through a proximal end of the guard member for allowing the attachment of the delivery member, to a mixed position, in which the medicament container holder is displaced distally in relation to the housing, at which mixed position the guard member locking device is activated and released by a proximal area of the housing, whereby the guard member is forced in the proximal direction by the force member for covering the delivery member.

2. The medicament delivery device of claim 1, wherein the first engagement members comprise resiliently movable hooking arms, the second engagement members comprise a ledge, and a proximal end surface of the housing is arranged to move the hooking arms out of engagement with the ledge when moved in contact with the hooking arms.

3. The medicament delivery device of claim 1, wherein the mixing guard mechanism comprises a first connection device interactively connecting the housing and the medicament container holder for allowing the medicament container holder to be displaced within the housing.

4. The medicament delivery device of claim 3, wherein the first connection device comprises cooperating threads on the housing and the medicament container.

5. The medicament delivery device of claim 1, further comprising a second guard member locking device interactively connected to the medicament container holder and to the guard member and configured to be positioned in a first unlocked state, in which the guard member is allowed to be distally displaced compressing the force member such that a proximal part of the delivery member protrudes through the proximal end of the guard member, and in a second locked state, in which the guard member is locked after the guard member is proximally displaced by the force member and covers the delivery member.

6. The medicament delivery device of claim 5, wherein the second guard member locking device comprises arms with hooks arranged to the medicament container holder and at least one rib having a distally directed end surface arranged to the guard member, such that when the guard member is moved proximally, at least one hook passes an end surface of the at least one rib, thereby preventing subsequent distal displacement of the guard member.

7. The medicament delivery device of claim 1, further comprising a drive mechanism arranged within the housing and configured to drive a stopper within the multi-chamber container.

8. The medicament delivery device of claim 7, wherein the drive mechanism comprises a plunger rod and a force member operatively acting on the plunger rod for urging the plunger rod in the proximal direction.

9. The medicament delivery device of claim 8, further comprising a holding device configured to hold the drive mechanism in a pre-tensioned state.

10. The medicament delivery device of claim 9, further comprising an activation mechanism configured to act on the holding device for releasing the drive mechanism from the pre-tensioned state.

11. The medicament delivery device of claim 1, wherein the medicament delivery device is an injection device.

* * * * *